(12) United States Patent
Studer

(10) Patent No.: US 8,123,349 B2
(45) Date of Patent: Feb. 28, 2012

(54) AUTOMATIC IMAGE COLOR AND CONTRAST OPTIMIZATION SYSTEM BASED ON CARTRIDGE IDENTIFICATION

(75) Inventor: Anthony D. Studer, Albany, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1429 days.

(21) Appl. No.: 11/700,674

(22) Filed: Jan. 31, 2007

(65) Prior Publication Data
US 2008/0180494 A1    Jul. 31, 2008

(51) Int. Cl.
*B41J 3/36* (2006.01)
(52) U.S. Cl. ........................................ 347/109
(58) Field of Classification Search ............ 347/14, 347/15, 19, 85, 109; 346/143; 400/88; 358/2.1, 358/3.06, 3.3, 523
See application file for complete search history.

(56) References Cited

U.S. PATENT DOCUMENTS

| | | | |
|---|---|---|---|
| 3,705,950 A | 12/1972 | Jirka et al. | |
| 4,211,012 A | 7/1980 | Alles et al. | |
| 4,372,695 A | 2/1983 | Ross | |
| 4,539,906 A | 9/1985 | Ogura | |
| 5,020,928 A | 6/1991 | Akiyama et al. | |
| 5,028,934 A | 7/1991 | Kasai et al. | |
| 5,052,832 A | 10/1991 | Akiyama et al. | |
| 5,083,122 A | 1/1992 | Clark | |
| 5,634,730 A | 6/1997 | Bobry | |
| 5,685,651 A | 11/1997 | Hayman et al. | |
| 5,748,342 A * | 5/1998 | Usami ............................ | 358/500 |
| 5,784,959 A | 7/1998 | Larios | |
| 5,825,995 A | 10/1998 | Wiklof et al. | |
| 5,861,877 A | 1/1999 | Kagayama et al. | |
| 5,918,989 A | 7/1999 | Stout, Jr. et al. | |
| 6,113,293 A | 9/2000 | Schanke et al. | |
| 6,229,565 B1 | 5/2001 | Bobry | |
| 6,261,011 B1 | 7/2001 | Day et al. | |
| 6,338,555 B1 | 1/2002 | Hirose | |
| 6,359,640 B1 | 3/2002 | Ravitz et al. | |
| 6,398,432 B1 | 6/2002 | Day et al. | |
| 6,499,840 B2 | 12/2002 | Day et al. | |
| 6,517,266 B2 | 2/2003 | Saund | |
| 6,641,313 B2 | 11/2003 | Bobry | |
| 6,674,543 B2 | 1/2004 | Day et al. | |
| 6,769,360 B2 | 8/2004 | Walling | |
| 6,991,332 B1 | 1/2006 | Fan et al. | |
| 6,999,113 B1 | 2/2006 | Omura | |
| 7,014,301 B2 * | 3/2006 | Dentel et al. ............ | 347/85 |
| 7,070,347 B2 | 7/2006 | Carriere et al. | |
| 7,073,717 B1 | 7/2006 | Arnold et al. | |
| 7,524,051 B2 * | 4/2009 | Ahne et al. ............ | 347/109 |
| 7,619,776 B2 * | 11/2009 | Writt et al. ............ | 358/3.06 |
| 2004/0022571 A1 | 2/2004 | Walling | |
| 2004/0238640 A1 | 12/2004 | Gold et al. | |
| 2005/0083357 A1 | 4/2005 | Silverbrook | |
| 2005/0135857 A1 | 6/2005 | Saund et al. | |
| 2005/0201809 A1 | 9/2005 | Silverbrook | |

(Continued)

FOREIGN PATENT DOCUMENTS

| | | |
|---|---|---|
| EP | 0 258 792 A2 | 3/1988 |
| JP | 61064469 | 4/1986 |
| JP | 10035028 | 2/1998 |

(Continued)

*Primary Examiner* — Anh T. N. Vo

(57) ABSTRACT

A hand-held printer includes an ink supply and a graphical interface configured to display a preview of an image prior to printing and wherein the image preview is displayed on the graphical interface in a color format based on the color capability of the ink supply.

20 Claims, 2 Drawing Sheets

U.S. PATENT DOCUMENTS

| | | |
|---|---|---|
| 2005/0286090 A1 | 12/2005 | Ahne et al. |
| 2006/0024114 A1 | 2/2006 | Lyman et al. |
| 2006/0050131 A1 | 3/2006 | Breton |
| 2006/0051150 A1 | 3/2006 | Klein |
| 2006/0114487 A1 | 6/2006 | Caveney, Jr. et al. |

FOREIGN PATENT DOCUMENTS

| | | |
|---|---|---|
| WO | WO 9105665 | 5/1991 |
| WO | WO-2004056577 | 7/2004 |
| WO | WO-2006060228 | 6/2006 |

\* cited by examiner

AUTOMATIC IMAGE COLOR AND CONTRAST OPTIMIZATION SYSTEM BASED ON CARTRIDGE IDENTIFICATION

BACKGROUND

Handheld printers are generally compact, portable printing devices used for printing text and/or graphics onto a variety of media, including but not limited to, paper, envelopes, packages, or even walls. Handheld printers generally include a memory or control device and at least one ink supply or reservoir having either a mono, dual or multi-color printing capability. In general, images are loaded from a computer or other external source into the handheld printer through a communications interface. In some cases, handheld printers include mono or full color graphical interfaces, which provide the user with the capability to preview the images prior to printing. A shortcoming with known graphical interfaces, however, is that they fail to provide the user with an accurate representation of the color of the image that will be printed using the particular ink supply that is installed. For example, if a blue image is loaded into a handheld printer having a full color display and a red ink supply, the image previewed in the graphical interface will generally represent the blue image as loaded and saved into the memory of the handheld printer, despite that fact the red ink supply is incapable of printing the image in that color. Moreover, known handheld printers provide no indication to the user that the preview image will print in a color other than what is shown in the graphical interface. The embodiments described hereinafter were developed in light of these and other drawbacks associated with handheld printing devices.

BRIEF DESCRIPTION OF THE DRAWINGS

The present embodiments will now be described, by way of example, with reference to the accompanying drawings, in which.

DETAILED DESCRIPTION

A system and method for printing text and graphics with a handheld printer is provided. The handheld printer includes a graphical interface, a memory for storing one or more images, at least one ink supply containing one or more colors of ink, and at least one communications interface. The ink supply can be an ink cartridge, a toner cartridge, a dye sublimation ribbon, or other supply appropriate for a given application. The communications interface can be a wired or wireless interface, capable of transmitting and receiving images, as well as instructions, commands and other data. Further, the communications interface can be a media slot, capable of receiving removable media, such as a memory card, on which images may be transferred. The ink cartridge includes a cartridge ID readable by the handheld printer, from which the printer can determine the printing capabilities of the cartridge. The graphical interface displays information to the user, and allows the user to preview an image prior to printing. The preview image is presented to the user in a color and contrast which is selected by the handheld printer, based on the capabilities of the installed ink cartridge. The printer determines the capabilities of the installed ink cartridge by reading the associated cartridge ID. The printer continuously monitors the installed cartridge to determine the colors and contrast levels the printer is capable of printing. The images, without limitation, can consist of pictures, text, graphics, and combinations thereof. Images stored can have any color format, including grayscale, black and white, mono-color, and full color. The color scheme in which the images are stored is referred to hereinafter as the "primitive" color. If the user wishes to print a stored image, and the primitive color for that image is incompatible with the installed cartridge, the user will be notified, such as through a textual or graphical prompt on the graphical interface. The user will then be presented with the printing options available through the currently installed cartridge. Available printing options include, without limitation, mono-color printing, full color printing and gray-scale imaging. If the cartridge is capable of printing in the primitive image color, but is also capable of printing in additional colors, the user will have the option of changing the chosen color.

Figures 1, 1A:
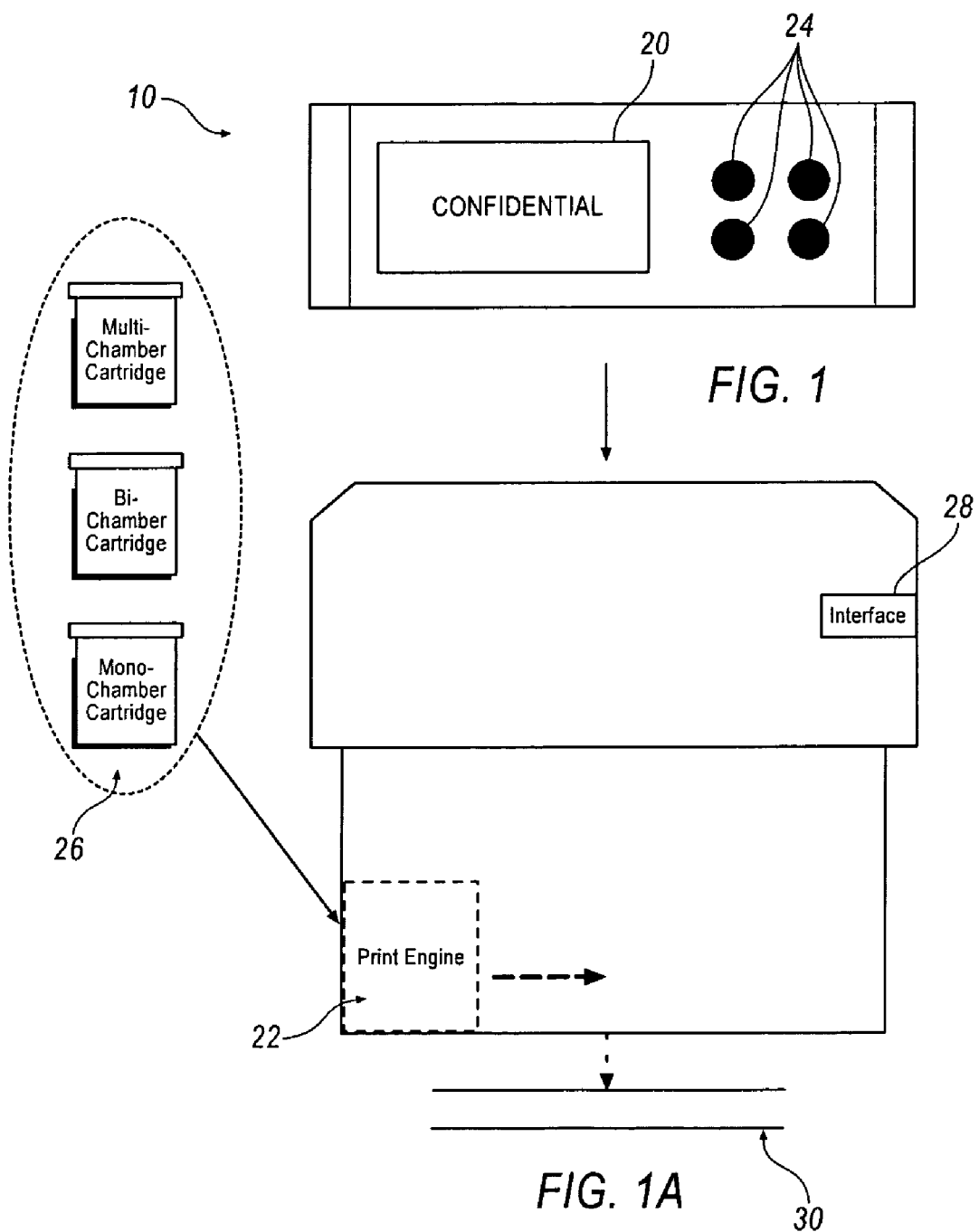
FIG. 1 illustrates an exemplary handheld printer, according to an embodiment.

An embodiment of the present disclosure will now be described by way of example with reference to the attached figures. One of ordinary skill in the art understands that the specific configuration of components in FIG. 1 is exemplary. For example, FIG. 1 illustrates a stamp type handheld printer. However, alternate embodiments could as easily encompass many other forms, such as a motor-driven, or actuator-driven handheld printer, a swipe-type handheld printer, a hand-top mounted handheld printer, one that is simply held in the user's hand or a gun style handheld printer.

FIGS. 1 and 1A illustrate a top view and a side view, respectively, of an exemplary handheld printer 10. The handheld printer 10 includes a graphical interface 20 and user inputs 24 useful for interacting with information displayed on the graphical interface 20. A print carriage 22 is provided, which houses a print cartridge 26, and is operative to print an image on media 30, such as paper. The print cartridge 26 could be a mono-color cartridge, capable of printing in a single ink color, or may be capable of printing in two or more colors. Additionally, the print cartridge 26 could be a toner cartridge, dye sublimation ribbon, or other appropriate ink supply without parting from the scope of this disclosure. A communications interface 28 allows information and images to be exchanged between the printer 10 and an external source, such as a computer (not shown), and allows transmitted images to be stored in memory (not shown) on handheld printer 10. The communications interface can be a wired or wireless interface, capable of transmitting and receiving images, as well as instructions, commands and other data. Further, the communications interface can be a media slot, capable of receiving removable media, such as a memory card. Connection to the external source can be made through any suitable connection medium including but not limited to, a USB cable, an infrared (IR) connection, or a wireless connection. The handheld printer 10 further includes a printer controller (not shown) operative, for example, to control the functionality of handheld printer 10, and to adjust image properties based on the capabilities of the installed ink cartridge 26. The printer controller may include a series of software algorithms configured to perform various functions internal to the printer, including reading the cartridge ID, analyzing image data to determine primitive color formats and providing additional color format options.

Upon a power-up condition, the printer 10 detects whether a print cartridge 26 is installed. If there is a cartridge 26 installed, the printer 10 reads the cartridge ID and determines the color or colors in which the cartridge 26 is capable of printing. While in operation, the printer 10 monitors the cartridge ID to detect whether cartridge 26 is removed and replaced with another cartridge. If a cartridge 26 is replaced, the printer 10 detects the capabilities of the newly installed cartridge 26 by reading the associated cartridge ID.

Images stored in memory can be displayed on the graphical interface 20 in any form, including but not limited to, a series of thumbnail images or in textual form such as a list of saved files. If the images are presented to the user in an image form, as opposed to textually, the specific graphical representation of the image is determined based on the capabilities of both the installed cartridge 26 and the graphical interface 20. The printer controller analyzes the stored images to determine the color format in which the images are saved (the "primitive" color). The primitive color format can be anything from a mono-color image, to a gray-scale image, to a full color image. The primitive color format is compared to the color formats available through the installed cartridge 26. If the installed cartridge 26 is capable of reproducing an image in the primitive color format, then the printer 10 will display the image on the graphical interface 20 using the primitive color format. On the other hand, if the ink cartridge 26 is not capable of reproducing the image in the primitive color format, the printer 10 will display the image on the graphical interface 20 in an "optimal" color format.

The optimal color format is determined by the printer controller based on the capabilities of the installed cartridge 26. Specifically, each image is stored in the primitive RGB color scheme, and then color maps for each type of cartridge are pre-programmed into the controller. When a cartridge 26 is installed, the printer automatically selects the associated color map for the installed cartridge 26. When an image is selected for printing, the primitive color scheme is converted to the closest matching color map (i.e., the optimal color format). The number of color formats available from a given cartridge 26 is determined by the controller based on the cartridge ID, and is dependent on the number of colors available with the cartridge 26. For instance, a monocolor cartridge may have a single color format, such as a black and white format, or may have a second available format, such as a gray-scale format. A cartridge 26 having two available colors may have color formats using each of the colors individually, as well as formats using a combination thereof. As a cartridge 26 is provided having more available colors, the number of possible color formats available using that cartridge 26 increases. As stated previously, the user has the option at any time of swapping the installed cartridge 26 for another. Thus, if the user desires additional or different color formats, the user can simply swap the cartridge 26 at any time. In so doing, the printer controller will again read the cartridge ID of the newly installed cartridge 26 and update the optimal color format based on the newly identified capabilities.

Accordingly, images are presented to the user in a color format determined by the print controller. The actual presentation of the image using this color format is further dependent on the capabilities of the graphical display 20. While a full color graphical display 20 can simply display the image in the format chosen by the printer controller, many printers 10 are not provided with full color displays 20. For those situations where the display 20 is not a full color display, another method must be used to indicate to the user the color format chosen by the print controller. The method of indicating the chosen color format to the user can include, for instance, a textual reference displayed on the graphical interface 20 at the same time as the displayed image.

Regardless of whether the graphical display 20 is a full color display or a mono-color display, the graphical display 20 may also include an indicator which is operable to indicate if the displayed image is being presented in a color format which differs from the primitive color format. The indicator could be, for example, a simple graphical indicator or textual prompt or various graphical textures (i.e. hash marks) representing different colors.

Once the images are displayed on the graphical interface 20, the user browses the stored images, and selects an image using user inputs 24. As described previously, this image is presented to the user in either the primitive color format, or in an optimal color format, determined by the printer controller based on the cartridge ID of the ink cartridge 26. When the user selects an image, further options may be presented to the user. While the image is presented using the primitive color format, or the optimal color format, the installed cartridge 26 may be capable of printing the image in additional color formats different than the displayed format. If the cartridge 26 is capable of printing the chosen image in additional color formats, the user may be presented with a series of additional representations of the chosen image, using additional available color formats. Additionally, the user still has the option of swapping the installed cartridge 26 with another cartridge 26 having additional or different color formats.

The foregoing will now be described by way of example. Assume the user has chosen to print an image which consists of a purple line drawing. Assume further that the cartridge 26 installed in the printer 10 is a mono-color cartridge capable of printing only in yellow. In this case, the printer controller will read the cartridge ID of the installed cartridge 26 and will determine that the optimal color format for the image is yellow. If the graphical display is a full color display, the graphical interface 20 will display a yellow line drawing. If the graphical interface 20 is a mono-color interface, the display will illustrate a line drawing, with an indicator that the image is to be printed in yellow. In either case, the graphical interface 20 may also display a prompt informing the user that the image is not displayed in the primitive image format, and may additionally indicate to the user what the primitive color is. Furthermore, the graphical interface 20 may indicate to the user an appropriate cartridge 26 which, if installed, would be capable of printing the image in the primitive color. For example, in the example above, the graphical interface 20 may indicate to the user that the primitive color format could be reproduced using, for example, a mono-color cartridge capable of printing in purple, a bi-color cartridge capable of printing in red and blue, or a full-color cartridge.

As a second example, assume again that the user chooses to print a purple line drawing. Assume for this example that the installed cartridge 26 is a bi-color cartridge capable of printing in yellow or blue. The printer controller would determine from the cartridge ID that the installed cartridge is capable of reproducing an image at least in yellow and in blue, as well as potentially in green. The controller would determine the optimal color format. In this example, the printer might choose blue as the closest match for purple. The image would then be displayed to the user on a full color graphical interface 20 as a blue line drawing, or as a line drawing with an indicator that it is blue on a monocolor graphical interface 20. The user may also be presented with a prompt indicating that the image shown is not in the primitive format. When the user chooses the image, further printing options may also be presented to the user on the graphical interface 20 due to the additional color formats available using the installed cartridge 26. Additional color formats presented could include a yellow line drawing, or a green line drawing.

Figure 2:
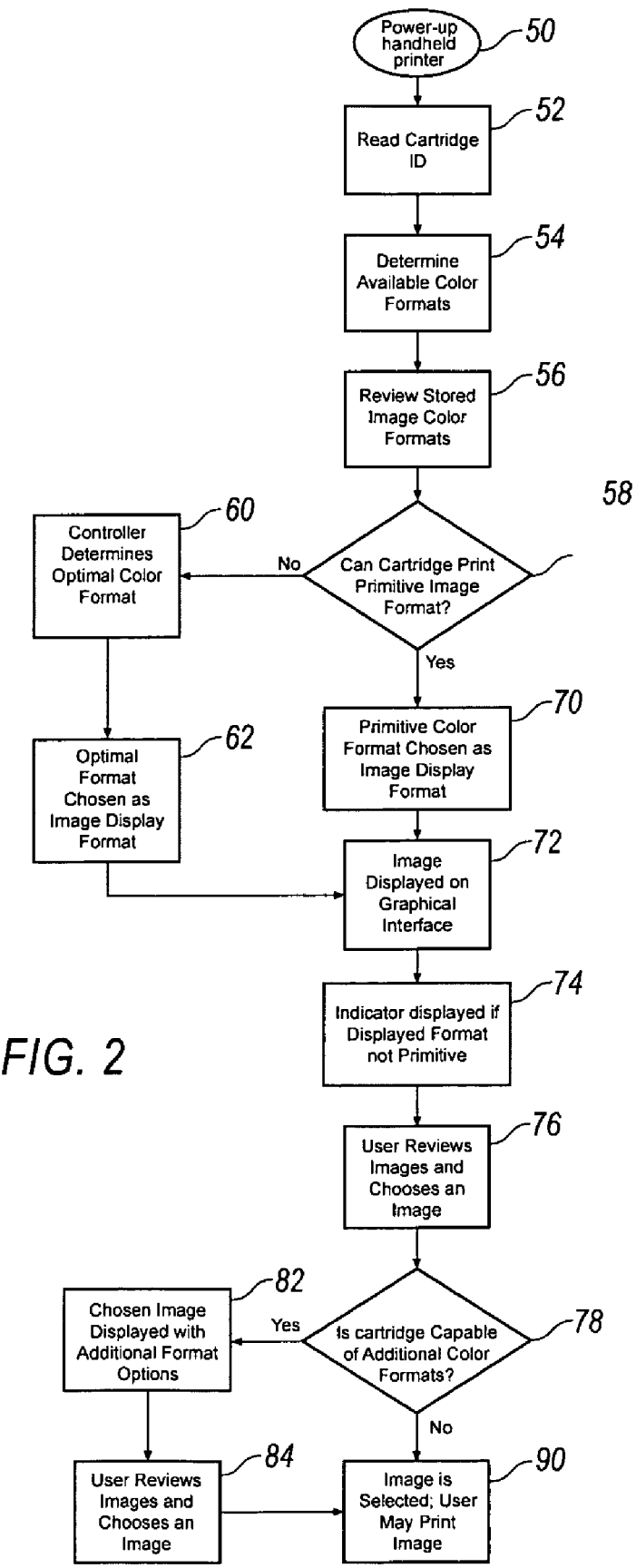
FIG. 2 is a flow diagram illustrating an exemplary handheld printing method, according to an embodiment.

FIG. 2 is a flow diagram illustrating an exemplary printing method according to an embodiment of handheld printer 10. The exemplary process assumes that an image has already been loaded into the memory of the handheld printer 10.

At step 50 the user powers-up the handheld printer 10. At step 52, the printer reads the Cartridge ID, and determines at step 54 the color formats in which the printer is capable of printing. At step 56, the printer controller reviews the stored images to determine the primitive image formats. The printer controller then compares the primitive image formats at step 58 with available cartridge image formats based on the cartridge ID. If the installed cartridge is capable of reproducing an image in the primitive color format, the primitive color format is chosen at step 70 as the format in which the image will be displayed. If the installed cartridge is not capable of reproducing the image in the primitive image format, the controller determines the optimal color format at step 60, by choosing the available color format which most closely matches the primitive image format images stored in memory. The optimal format is then chosen at step 62 as the format in which the image will be displayed. Once the controller determines the format in which images will be displayed, the images are displayed to the user on the graphical interface at step 72. If a displayed image is not displayed using the primitive format, an indicator so indicates on the graphical display, as shown in step 74. Step 76 indicates the action of the user in scrolling through the displayed images, and choosing an image. If at step 78 it is determined that the installed cartridge is capable of printing the chosen image in other color formats in addition to the optimal or primitive color format, the user is provided with the additional color format options at step 82. The user may review, at step 84, the additional color format options and choose a format therefrom. In either case, when the user has chosen an image and a color format, the user may choose to print the image at step 90.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

In general, the foregoing description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

What is claimed is:

1. A hand-held printer, comprising:
an ink supply, said printer being programmed to determine a color capability of said ink supply;
a print engine of said printer for printing an image using ink received from said ink supply; and
a graphical interface of said printer that is configured to display a preview of the image prior to printing; wherein said image preview is displayed on said graphical interface in a color format indicative of what color or colors can be used to print the image based on the color capability of said ink supply.

2. The printer of claim 1, wherein said ink supply is an ink cartridge and includes a cartridge ID that identifies the color capability of said ink supply.

3. The printer of claim 1, further comprising a memory in communication with said print engine for storing images and information in said hand-held printer.

4. The printer of claim 1, wherein said color format is a primitive color format.

5. The printer of claim 1, wherein said color format is an optimal color format.

6. The printer of claim 1, further comprising user input devices associated with said graphical interface, wherein a user can operate said user input devices to select an optimal color format based on the color capability of said ink supply.

7. The printer of claim 1, wherein said graphical interface is programmed to display a prompt indicating that said image preview does not represent a primitive color format in which said image was saved.

8. The printer of claim 7, wherein said prompt further indicates the color format in which said image was saved.

9. The printer of claim 8, wherein said prompt indicates a different ink supply, which if installed, would print the color format in which the image was saved.

10. The printer of claim 1, further comprising one or more communication interfaces for exchanging data between said hand-held printer and an external device.

11. A method of printing an image of a hand-held printer, the method compring:
determining a color capability of an ink supply within the hand-help printer;
comparing the color capability of said ink supply to a primitive color of the image; and
displaying a preview of said image on a graphical interface, wherein said image preview is based upon the color capability of said ink supply.

12. The method of claim 11, further including selecting an optimal color format.

13. The method of claim 12, wherein selecting an optimal color format includes comparing the color capability of said ink supply to the primitive color of said image to determine the closest color match.

14. The method of claim 11, further including displaying a prompt to a user that indicates when said image preview is displayed in a color other than said primitive color.

15. The method of claim 11, further including displaying a prompt to a user that indicates said primitive color.

16. The method of claim 11, further including displaying a prompt to a user that indicates an ink supply which, if installed, would produce the color format in which the image is saved.

17. The method of claim 11, further comprising determining if said ink supply is capable of printing additional colors.

18. The method of claim 11, further comprising selecting a color for said image that is different from the color format of said image preview, wherein said color selection is based upon the color capability of said ink supply.

19. The method of claim 11, further comprising transmitting data between a communications interface and an external device.

20. The method of claim 11, wherein the ink supply is an ink cartridge.

* * * * *

UNITED STATES PATENT AND TRADEMARK OFFICE
CERTIFICATE OF CORRECTION

PATENT NO.        : 8,123,349 B2
APPLICATION NO.   : 11/700674
DATED             : February 28, 2012
INVENTOR(S)       : Anthony D. Studer It is certified that error appears in the above-identified patent and that said Letters Patent is hereby corrected as shown below:

In column 6, line 32, in Claim 11, delete "compring:" and insert -- comprising: --, therefor.

In column 6, line 34, in Claim 11, delete "hand-help" and insert -- hand-held --, therefor.

Signed and Sealed this
Sixth Day of November, 2012

David J. Kappos
*Director of the United States Patent and Trademark Office*